United States Patent [19]

Flynn

[11] Patent Number: 5,327,910
[45] Date of Patent: Jul. 12, 1994

[54] THERAPEUTIC DEVICE FOR MALE SEXUAL DYSFUNCTION

[75] Inventor: Darcy L. Flynn, Bluewater Beach, Australia

[73] Assignee: S & T No 27 Pty Ltd, Australia

[21] Appl. No.: 778,961

[22] PCT Filed: Jun. 27, 1990

[86] PCT No.: PCT/AU90/00272

§ 371 Date: Dec. 27, 1991

§ 102(e) Date: Dec. 27, 1991

[87] PCT Pub. No.: WO91/00073

PCT Pub. Date: Jan. 10, 1991

[30] Foreign Application Priority Data

Jun. 29, 1989 [AU] Australia ............... 37146/89
Jun. 29, 1989 [AU] Australia ............... 37147/89

[51] Int. Cl.⁵ ................... A61F 6/02; A61F 5/00
[52] U.S. Cl. ..................... 128/842; 600/38
[58] Field of Search ........... 128/842, 844, 918, 885; 604/347–353, 330; 600/39, 40, 38

[56] References Cited

U.S. PATENT DOCUMENTS

| | | |
|---|---|---|
| 2,581,114 | 1/1952 | Larson . |
| 2,618,270 | 11/1952 | Pearson ............... 128/885 |
| 2,756,753 | 7/1956 | Means ................. 128/885 |
| 2,818,855 | 1/1956 | Miller . |
| 3,511,230 | 5/1970 | Strong . |
| 3,636,948 | 1/1972 | Atchley . |
| 3,705,580 | 12/1972 | Gauthier . |
| 3,794,020 | 2/1974 | Bagby . |
| 4,139,007 | 2/1979 | Diamond ............... 128/842 |
| 4,203,432 | 5/1980 | Koch . |
| 4,880,016 | 11/1989 | Worth ................... 128/885 |
| 4,942,886 | 7/1990 | Timmons .............. 128/885 |
| 5,065,744 | 11/1991 | Zusmanovsky ..... 128/842 |
| 5,074,315 | 12/1991 | McCuiston ........... 128/844 |

FOREIGN PATENT DOCUMENTS

| | | |
|---|---|---|
| 1014983 | 5/1983 | Australia . |
| 37146-89 | 4/1990 | Australia . |
| 0336834 | 5/1921 | Fed. Rep. of Germany ...... 128/885 |
| 734394 | 7/1955 | United Kingdom . |
| 1545587 | 5/1979 | United Kingdom . |
| 83-01574 | 5/1983 | World Int. Prop. O. . |
| 88/01856 | 3/1988 | World Int. Prop. O. . |

*Primary Examiner*—Michael A. Brown
*Attorney, Agent, or Firm*—Larson and Taylor

[57] ABSTRACT

A therapeutic device (20) for the treatment of male sexual dysfunction which has first and second substantially rigid portions (21,23) interconnected by malleable or deformable portions (24). The device (20) is fitted to the base of the male penis and by selective deformation of the device (20), the first portion constricts blood flow through the penile veins to enable the user to achieve a penile erection; the second portion (23) constricts the urethra to prevent premature ejaculation; and the malleable or deformable portions (24) constrict blood flow through the penile arteries to overcome Priapism. The device (20) has a core (30) (e.g. of copper wire) within a deformable resilient sheath (33), with grooves or slots (27) which allow blood flow through the blood vessels under the skin of the penis when in use.

14 Claims, 3 Drawing Sheets

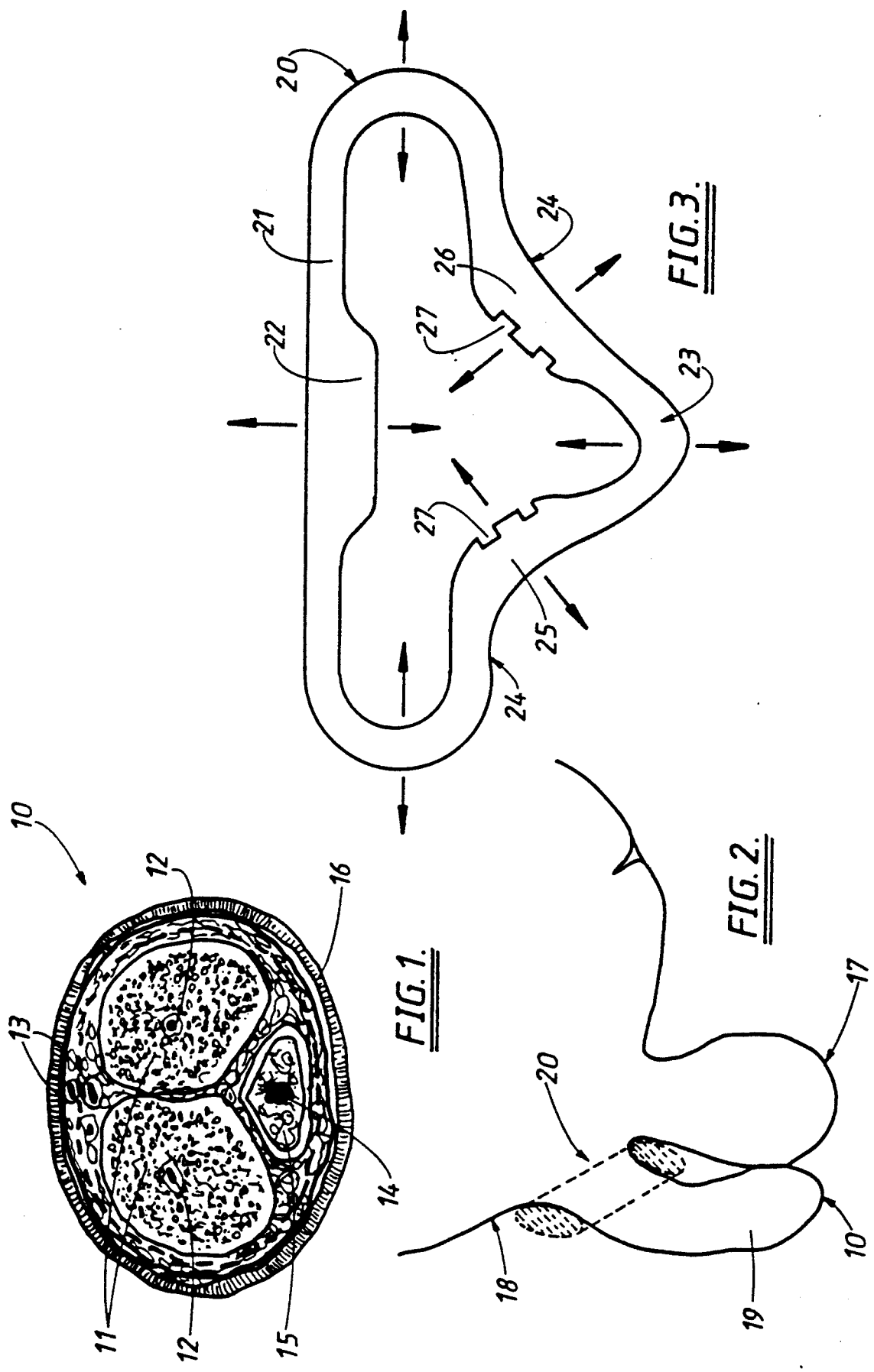

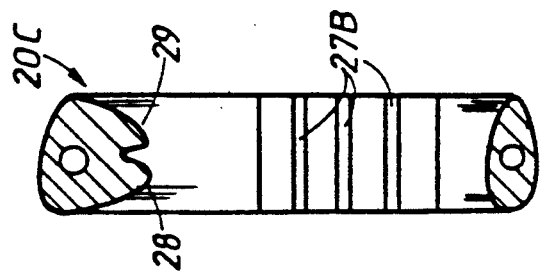
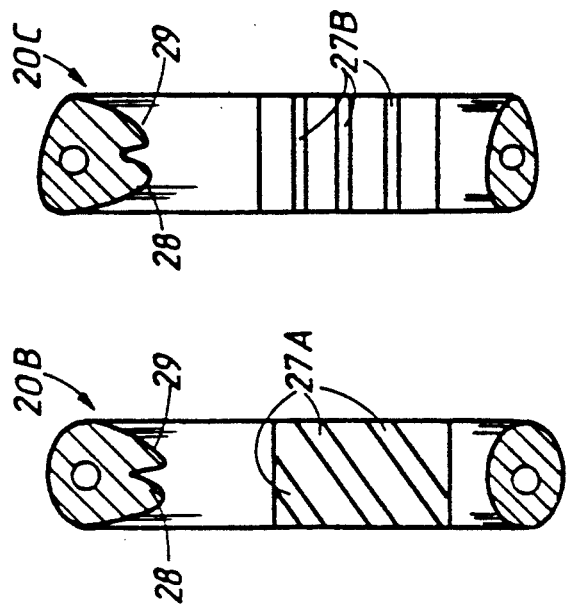
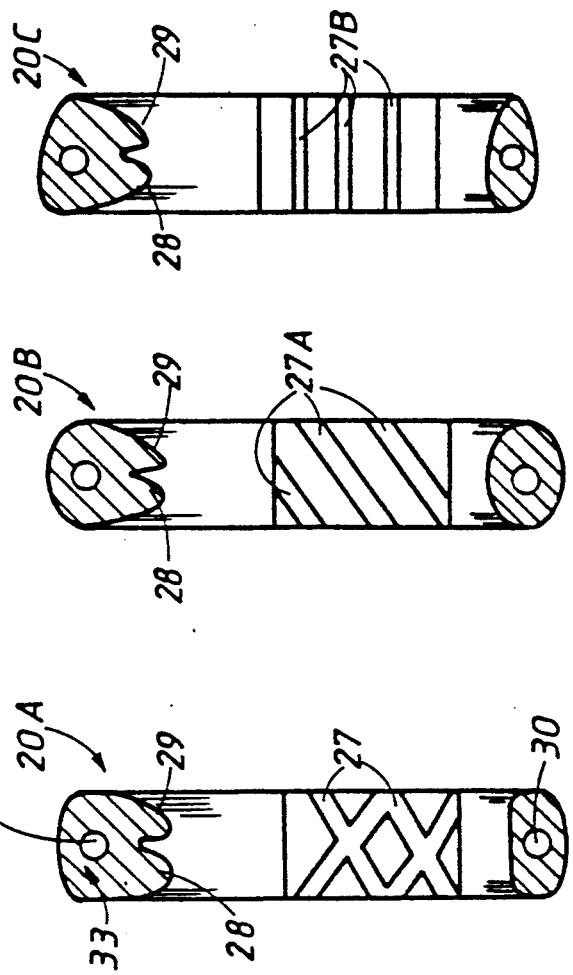
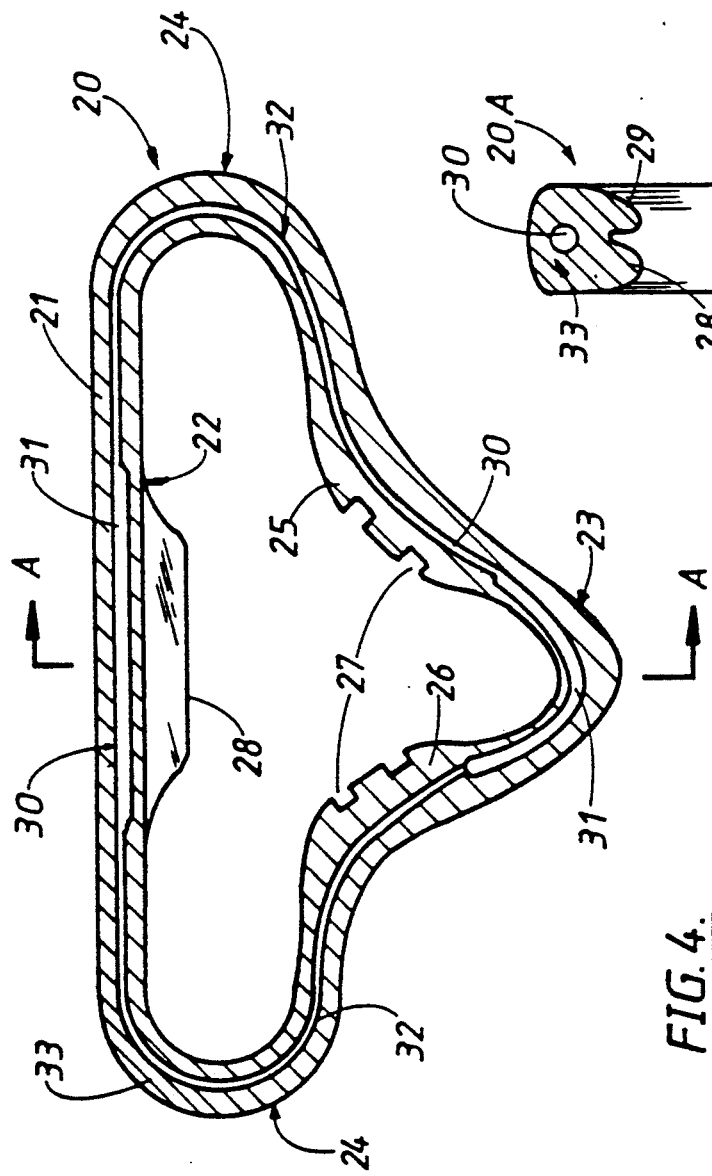

THERAPEUTIC DEVICE FOR MALE SEXUAL DYSFUNCTION

BACKGROUND OF THE INVENTION (1) Field of the Invention

This invention relates to a therapeutic device for male sexual dysfunction. The device may also be used to enhance male sexual pleasure (e.g. by prolonging the male orgasm).

(1) Prior Art

There are three main problem areas in male sexual dysfunction, as follows:
 (1) the inability to achieve and/or maintain penile erection;
 (2) Priapism (i.e. where penile erection is not released); and
 (3) premature ejaculation, There are many reasons for these problems. In certain cases they are related to the side effects of drugs. Males who suffer arterial disease, renal disease and/or diabetes are also likely candidates to suffer such problems.

Various methods have been adopted in an attempt to solve these problems. For example, the problem of penile erection has seen the use of surgery to restore arterial flow and the use of inflatible implants to enable an erection to be achieved, Priapism often requires an injection to enable the erection to be released while desensitizing preparations can be prescribed for premature ejaculation.

All of the proposals to date have problems in themselves and tend to mitigate against any enjoyment obtained from performing the sexual act.

SUMMARY OF THE INVENTION

It is an object of the present invention to provide a device which may be used to solve (or reduce) one or more of the problems discussed above.

It is a preferred object to provide a device which can be fitted by the user as required.

It is a further preferred object to provide a device which is not obtrusive and which can be easily adjusted by the user to be both effective and comfortable.

It is a still further preferred object that the device will maintain feeling in the skin of the penis.

Other preferred objects of the present invention will become apparent from the following description.

In a broad aspect the present invention resides in a therapeutic device for male sexual dysfunction including:

a body having at least one rigid or semi-rigid portion and at least one malleable or deformable portion, so arranged that the body may be positioned around the base of a penis to apply a constriction force on at least one portion of the penis.

The body may comprise a closed loop. Alternatively, the body may be substantially C-shaped and the free ends of the body may be releasably engageable.

Preferably the body comprises a core within a sheath of deformable material, the sheath preferably being formed of plastics material and may be skin coloured and have a textured finish.

The core may be formed from copper or stainless steel wire or strip, plastics strip or the like. The rigid/semi-rigid portion(s) may be formed by placing a tubular portion about the wire or strip; or winding wire about the wire or strip; or by internal reinforcement or tempering of the wire or strip. The malleable or deformable portion may comprise the wire or strip or a reduced thickness/diameter section of same.

Preferably there are two opposed rigid/semi-rigid portions, the upper being substantially linear to bear on the top of the base of the penis and the lower of substantially U- or V-shape to span the urethra at the base of the penis.

Preferably the two rigid/semi-rigid portions are interconnected by the malleable/deformable positions, each of which may comprise textured sections to allow blood flow through the blood vessels just below the penile skin.

The textured sections may have diagonal, longitudinal or criss-crossed lines or slots.

The device may be substantially triangular in plan, although circular, oval, square, hexagonal or other shapes may be produced before the user forms the device to the desired shape to suit his needs. The device may be circular or oval in cross-section; or substantially triangular in cross-section, tapering towards the front of the device.

BRIEF DESCRIPTION OF THE DRAWINGS

To enable the invention to be fully understood, a preferred embodiment will now be described with reference to the accompanying drawings, in which:

FIG. 1 is a cross-sectional view of a male adult penis;

FIG. 2 is a schematic side view showing the location of the device in use;

FIG. 3 is a front view of the device;

FIG. 4 is a sectional front view of the device;

FIGS. 5 to 7 are sectional side views, taken on line A—A on FIG. 4 of alternative cross-sections of the device;

DETAILED DESCRIPTION OF THE PREFERRED EMBODIMENTS

Figure 11:
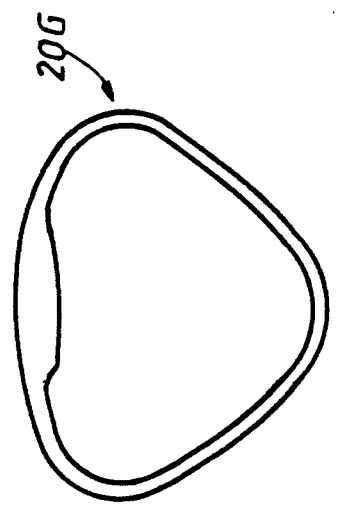
FIGS. 10, 11 and 12 are front views of further alternative embodiments of the device.

Referring to FIG. 1, the male penis 10 has the following areas relevant to the invention: corpora cavernosa 11, penile arteries 12, penile veins 13, urethra 14, corpus spongiosum 15 and skin 16. As shown in FIG. 2, the device 20 is positioned at the base of the penis 10 adjacent the scrotum 17.

The device 20, see FIGS. 3 and 4, is generally triangular in front view. The top portion 21 has an enlarged central section 22 opposed to the generally U- or V-shaped bottom portion. 23. The two side portions 24 have enlarged sections 25, 26 which have criss-cross slots or grooves 27 (see FIGS. 5 to 7) which allow blood flow through the blood vessels under the skin 16 of the penis 10 when the device 20 is in use. As shown in FIGS. 3 to 5, the central portion 22 has a pair of "lips" 28, 29 which apply spaced pressure to the top of the penis 10.

The device 20 has a core 30 of copper or stainless steel wire which is circular in section 31 in the central section 24 of the top portion and in the bottom portion 23, so arranged that these are rigid or substantially rigid. The remaining portions 32 of the core are flattened to form a thin-section strip which is malleable or deformable so that the shape of the device 20 can be changed as hereinafter described.

The core 30 is enclosed within a deformable plastic sheath 33 which is skin coloured (in a range of skin tones) and has a textured surface or "skin".

The user positions the device as shown in FIG. 2. If the dysfunction to be overcome is the problem of achieving and/or maintaining a penile erection, he deforms the side portion 24 so that the central section 22 (and its lips 28, 29) apply a pressure on the top of the penis 10 to constrict the flow through the penile veins 13 (including the deep Dorsal vein). When the flow through the arteries 12 exceeds the flow through the veins 13, erection will be achieved and maintained. As the bottom portion 23 does not constrict the urethra 14 (see FIG. 10), ejaculation can occur normally.

If the problem is Priapism, the enlarged sections 25, 26 of the side portions 24 are moved inwardly to constrict the arterial blood flow so that the veneous blood flow will enable the penis to become flaccid after erection.

For premature ejaculation, the bottom portion 23 is deformed to apply a constriction on the urethra 14.

As blood can flow through the blood vessels under the penile skin 16, penile feeling is not lost.

Referring to FIGS. 5 to 7, the cross-section of the devices 20A, 20B, 20C may be generally rectangulr (FIG. 5), circular or oval (FIG. 6) and triangular or tapered (FIG. 7). The lines or slots on the enlarged sections 25, 26 may be diagonal (27A) or longitudinal (27B).

Figure 8:
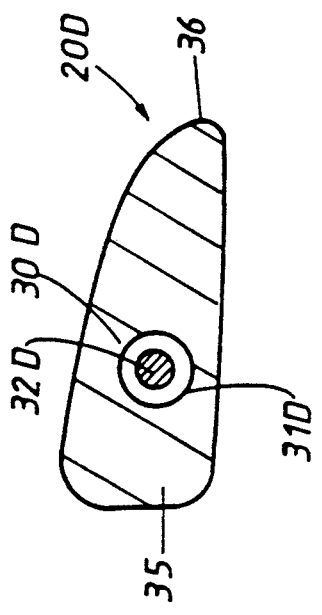
FIGS. 8 and 9 are respective sectional side views of further alternative cross-sections of the device.

Referring now to FIG. 8, the device 20D has a substantially right-angled triangular cross-section tapering from a back wall 35 which would engage the user's body 18 and tapering to a "nose" 36 a small distance along the shaft 19 of the penis 10.

In this embodiment, the core 30D is formed by copper or stainless steel wire and the rigid/semi-rigid sectin 31D are formed by winding wire around the core 30D, where the core forms the malleable section 32D.

Figure 9:
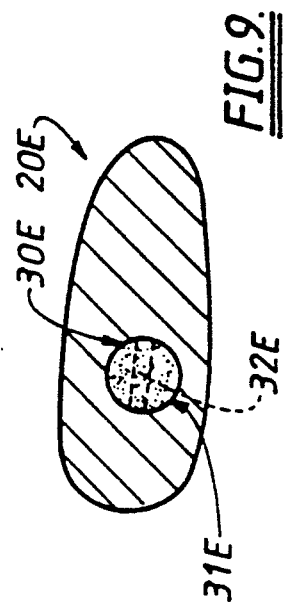

In the embodiment of FIG. 9, the device 20E has an oval cross-section with a core 30E formed of plastics (e.g. nylon, polyethylene) strip 32E where the enlarged sections 31E are of increased thickness and may be impregnated with glass reinforcing fibres.

Figure 10:
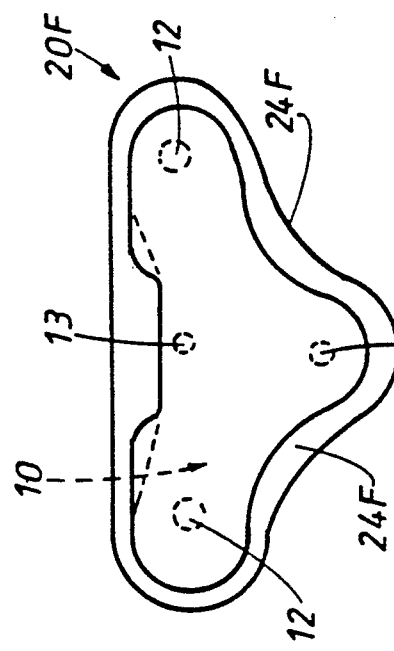

FIG. 10 shows an alternative embodiment of the device 20F which does not have the enlarged sections 25, 26 on its side portion 24F and the penis 10 is shown in dashed lines to show how the device can constrict the penile veins 13, while leaving the penile arteries 12 and urethra 14 unconstricted where the user has difficulty achieving and/or maintaining an erection.

FIG. 11 shows a further embodiment of the device 20G which is more circular in front view.

Figure 12:
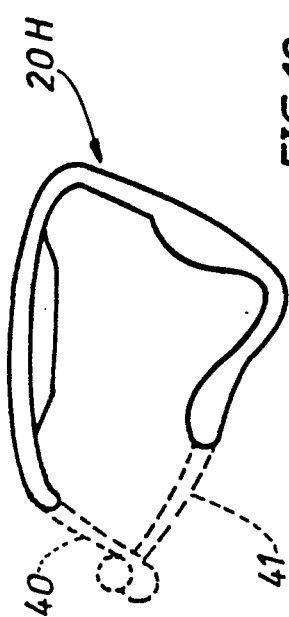

FIG. 12 shows a still further embodiment where the device 20H does not comprise a closed loop but is substantially C-shaped. As indicated by dashed lines 40, 41, the free ends of the device 20H may be releasably secured together to form a closed loop.

Once the user has established the best shape of the device for his needs, e.g. to achieve and maintain an erection without discomfort, he will leave the shape of the deviced fixed and it will be ready for use the next time the sexual act is to be consumated.

Because the sheath is preferably skin coloured and textured, it is unobtrusive and a sexual partner may not be aware that it is in place. The device can be easily fitted before the sexual act and removed when no longer required. It's inert material sheath 33 can be easily cleaned between use.

It will be readily apparent to the skilled addresssee that the present invention provides a simple, effective means for overcoming what, to many men, is a major problem and each man can adjust the device to suit his own particular needs.

In addition, the device can be adjusted to enhance the intensity and/or duration of orgasm to enhance the enjoyment of the sexual act.

To release the device, the side portions 24 may be pressed inwardly e.g. to move the top portion 21 outwardly and away from the penis 10.

Various changes and modifications may be made to the embodiments described and illustrated without departing from the scope of the present invention defined in the appended claims.

I claim:

1. A therapeutic device for the treatment of male sexual dysfunction, the device comprising a body to be positioned around the base of the penis, the body including:
    a first substantially rigid portion for, when the body is deformed so that the first portion exerts inward pressure, constricting blood flow through the penis veins, while permitting blood flow through the blood vessels under the penile skin,
    a second substantially rigid portion opposed to said first portion for, when the body is deformed so that said second portion exerts inward pressure, constricting the urethra while permitting blood flow through the blood vessels under the skin,
    and at least one malleable or deformable portion, interconnecting the first and second portions, for, when said malleable or deformable portion is deformed so as to exert inward pressure, constricting the blood flow through the penile arteries while permitting blood flow through the blood vessels under the penile skin.

2. A device according to claim 1 wherein:
the body comprises a closed loop.

3. A device according to claim 1 wherein:
the body comprises a core within a sheath of deformable material.

4. A device according to claim 3 wherein:
the sheath is formed of skin-coloured plastics material and has a textured finish or "skin".

5. A device according to claim 3 wherein:
the sheath has at least one portion of increased thickness and said at least one portion has a pair of lips to bear on the shaft of the penis and slots or grooves to enable blood flow through the blood vessels under the skin of the penis.

6. A device according to claim 1 wherein:
the first substantially rigid portion bears on the top of the penis and the second substantially rigid portion spans the urethra at the bottom of the penis, the second substantially rigid portion being substantially U- or V-shaped in front view.

7. A device according to claim 6 wherein:
the two substantially rigid portions are formed of copper or stainless steel wire; copper or stainless steel wire encased in a tube or around which wire is wound; or an enlarged section of glass-fibre-reinforced plastics.

8. A device according to claim 1 wherein:
the malleable or deformable portion or portions of the core are formed of copper or stainless, steel wire or strip; or plastics material wire or strip.

9. A device according to claim 1 wherein:

said body is substantially C-shaped so as to have free ends.

10. A device according to claim 9 wherein:
said free ends of said body are releasably engageable.

11. A device according to claim 1 wherein:
said first substantially rigid portion of said body includes a pair of lips which bear on the shaft of the penis.

12. A device according to claim 1 wherein:
said malleable or deformable portion includes slots or grooves therein to enable blood flow to the blood vessels under the skin of the penis.

13. A therapeutic device for the treatment of male sexual dysfunction, the device comprising a body to be positioned around the base of the penis, the body including:
 a first substantially rigid portion for, when the body is deformed so that the first portion exerts inward pressure, constricting blood flow through the penile veins, while permitting blood flow through the blood vessels under the penile skin,
 a second substantially rigid portion opposed to said first portion for, when the body is deformed so that said second portion exerts inward pressure, constricting the urethra while permitting blood flow through the vessels under the skin, and
 at least one malleable or deformable portion, interconnecting the first and second portions, for, when said malleable or deformable portion is deformed so as to exert inward pressure, constricting the blood flow through the penile arteries while permitting blood flow through the blood vessels under the penile skin, said first portion of said body including a pair of lips for bearing against the shaft of the penis and said malleable or deformable portion of the body including slots or grooves therein for permitting said blood flow through the blood vessels under the penile skin.

14. A therapeutic device for the treatment of male sexual dysfunction, the device comprising a body to be positioned around the base of the penis, the body including:
 a first substantially rigid portion for, when the body is deformed so that the first portion exerts inward pressure, constricting blood flow through the penile veins, while permitting blood flow through the blood vessels under the penile skin,
 a second substantially rigid portion opposed to said first portion for, when the body is deformed so that said second portion exerts inward pressure, constricting the urethra while permitting blood flow through the blood vessels under the skin, and
 at least one malleable or deformable portion, interconnecting the first and second portions, for, when said malleable or deformable portion is deformed so as to exert inward pressure, constricting the blood flow through the penile arteries while permitting blood flow through the blood vessels under the penile skin, said malleable or deformable portion of the body including slots or grooves therein for permitting said blood flow through the blood vessels under the penile skin.

* * * * *